United States Patent [19]

Muench et al.

[11] 3,959,365
[45] May 25, 1976

[54] SYNTHESIS OF D,1-LYSINE FROM 2-CYANOPYRIDINE

[75] Inventors: Terry G. Muench, Antioch, Calif.; George E. Ham, Lake Jackson, Tex.

[73] Assignee: The Dow Chemical Company, Midland, Mich.

[22] Filed: May 21, 1974

[21] Appl. No.: 471,949

[52] U.S. Cl. .......................... 260/534 L; 260/293.86
[51] Int. Cl.² .......................................... C07C 99/10
[58] Field of Search ................... 260/293.86, 534 L

[56] References Cited
OTHER PUBLICATIONS
Chem. Abstracts, 72:43610c, (1970).
Chem. Abstracts, 72:90319z, (1970).

Primary Examiner—G. Thomas Todd
Attorney, Agent, or Firm—Benjamin C. Colley

[57] ABSTRACT

A process for the preparation of d,1-lysine wherein 2-cyanopyridine is hydrolyzed to picolinamide, the picolinamide is hydrogenated to pipecolamide, the pipecolamide is converted to 1-acetyl-2-cyanopiperidine, the 1-acetyl-2-cyanopiperidine is then converted to a compound which is hydrolyzed to d,1-lysine.

8 Claims, No Drawings

SYNTHESIS OF D,1-LYSINE FROM 2-CYANOPYRIDINE

BACKGROUND OF THE INVENTION

This invention relates to a process for the preparation of d,l-lysine from 2-cyanopyridine.

It is known that lysine can be synthetically made from each of dihydropyran, caprolactam, piperidine, cyclohexanone and other starting materials.

U.S. Pat. No. 2,934,541 shows the preparation of lysine from piperidine.

SUMMARY OF THE INVENTION

It now has been found that d,l-lysine can be prepared from 2-cyanopyridine by hydrolyzing it to picolinamide, hydrogenating the picolinamide to pipecolamide, converting the pipecolamide to 1-acetyl-2-cyanopiperidine with acetic anhydride, reacting 1-acetyl-2-cyanopiperidine with a compound which yields ammonium ions or a mixture thereof with a compound which yields carbonate ions, and hydrolyzing the resulting product to d,l-lysine.

The 1-acetyl-2-cyanopiperidine intermediate in the above process is a new compound.

DETAILED DESCRIPTION

The starting material, 2-cyanopyridine is readily prepared from butadiene and cyanogen by the method reported by Janz et al. Can. J. Res. B25:272 (1947).

This starting material is hydrolyzed to picolinamide under conditions well known for conversion of nitriles to amides. Preferred is the catalytic hydrolysis, using catalysts such as copper salts or strong base ion exchange resins. Thus, an aqueous solution of the nitrile may be heated at 50°C to about 120°C in the presence of Dowex 21K (OH⁻) or Amberlite IRA 400 (OH⁻) for about 1 to 20 hours under autogenous pressure if the mixture is above its atmospheric boiling point. The weight ratio of catalyst to nitrile may vary from 0.1 to 2. After hydrolysis, the picolinamide may be isolated by filtering off the catalyst and distilling off the water, or the water solution may be used as is in the following reaction.

Picolinamide is hydrogenated to pipecolamide by the following conditions. To an aqueous solution of picolinamide is added the hydrogenation catalyst, the mixture is placed in a closed reaction vessel, pressured with hydrogen, and heated with agitation until the mixture ceases to absorb hydrogen. Suitable catalysts are Raney nickel, nickel suppoted or alumina, platinum, platinum oxide, rhodium or palladium. These are generally employed in a weight ratio of catalyst to picolinamide of 0.01 to 1.0. Hydrogenation pressures of 50 psi to 3000 psi are usually used; preferred are 100 psi to 1000 psi. Temperature may vary from 20°C to about 150°C and depends on the catalyst activity and amount employed. Nickel catalysts will generally require higher reaction temperatures, such as about 100°C or higher.

Pipecolamide is then converted to 1-acetyl-2-cyanopiperidine by heating it with an excess of acetic anhydride. The mole ratio of acetic anhydride to pipecolamide should be at least 3:1 and may be as high as 30:1, preferably about 4:1 to 10:1. The reaction time will depend on the temperature chosen and may be as long as 12 hours at about 100°C or as short as 30 minutes at about 170°C, preferably about 2–6 hours at about 130°–150°C.

The 1-acetyl-2-cyanopiperidine is then reacted with a compound which yields ammonium ions and a compound which yields carbonate ions under the following conditions to produce products which may be hydrolyzed to d,l-lysine. An aqueous solution of the reactants is heated at about 60° to 160°C for sufficient time to cause complete conversion of the 1-acetyl-2-cyanopiperidine, usually about 15 minutes to 24 hours. Suitable compounds yielding one or the other of the above ions are ammonium carbonate, ammonium bicarbonate, ammonia, carbon dioxide, ammonium chloride, ammonium acetate, sodium carbonate, sodium bicarbonate, potassium carbonate, potassium bicarbonate and ammonium cyanide. Mole ratios of these compounds to 1-acetyl-2-cyanopiperidine employed are generally 3:1 to 50:1 for compounds yielding ammonium ions and 3:1 to 40:1 for compounds yielding carbonate ions. The reaction may be performed in the presence of compounds yielding cyanide ions, e.g. HCN, alkali metal cyanides or alkaline earth metal cyanides, and when so performed, will result in increased yields of d,l-lysine after hydrolysis of the reaction product. Alternatively, the reaction may be performed in the presence of only ammonia or ammonium hydroxide, with or without added compounds which yield cyanide ions, to produce products which may be hydrolyzed to lysine.

The product from the above reaction is then hydrolyzed to d,l-lysine under the following conditions. Heating in the presence of an acid or a base is preferred, using for example, a strong acid such as hydrochloric acid or sulfuric acid; or a strong base such as the alkali metal hydroxides or alkaline earth metal hydroxides. At least six equivalents of acid or at least 4 equivalents of base should be used per mole of 1-acetyl-2-cyanopiperidine used in the previous reaction. At least 20 moles of water should be present per mole of 1-acetyl-2-cyanopiperidine used above. Reaction temperatures employed are generally in the range of 100°C to 200°C. Closed reaction vessels operating under autogenous pressure will be required for temperatures much above 100°C.

The following examples are presented solely to illustrate but not limit the invention.

EXAMPLE 1

26½ Grams (0.205 moles) of 2-cyanopyridine, 35 grams of Dowex 1-X₈ anion exchange resin (OH⁻ form) and 175 ml. water are placed in a reaction flask fitted with a reflux condenser and magnetic stirrer. After stirring briefly to dissolve the nitrile, the mixture is heated to reflux. After 3 hours and 15 minutes, the resin is filtered off and washed with 100 ml. of boiling water. The combined filtrates are evaporated under reduced pressure, and the resulting solid dried under vacuum at 80°C. An amount of 25.6 grams of picolinamide is obtained, corresponding to an 82% yield based on 2-cyanopyridine. A small amount recrystallized from benzenehexane melts at 107.0°–108.5°C.

Ten grams (0.082 moles) of picolinamide in 35 ml. water is hydrogenated using 3.0 grams of 5% rhodium-on-carbon as catalyst. A glass lined reactor is used. With an initial hydrogen pressure of 590 psi, the reaction is complete in 4 hours at 65°C, the pressure drop being 350 psi. The catalyst is filtered off and the water removed under reduced pressure to give 9.63 g. of pipecolamide, a 92% yield based on picolinamide. A small amount recrystallized from benzene melts at

145°–6°C.

An amount of 19.2 g. (0.15 moles) of pipecolamide is added portionwise to 102 g. (1.0 moles) of acetic anhydride over a 15 minute period with stirring. The temperature rises to ca. 60°C. The mixture is then heated to reflux, during which the solid dissolves and the solution turns a dark brown. After refluxing for 4 hours, the reaction mixture is subjected to vacuum distillation (first at 60 mm Hg to remove acetic acid and excess acetic anhydride, and then at 1–4 mm Hg pressure). Thus is obtained 15.3 grams of 1-acetyl-2-cyanopiperidine, boiling at 104°–14°C. This corresponds to a 67% yield based on pipecolamide.

An amount of 1.86 g. (0.0122 moles) of 1-acetyl-2-cyanopiperidine, 18 ml. of concentrated (58%) ammonium hydroxide and 6 ml. of water are mixed in a glass reactor. The mixture is then frozen in a dry ice-acetone bath, and 17 grams (ca. 0.39 moles) of dry ice is added to the reactor. The reactor is quickly assembled, purged and then pressurized to 200 psi with nitrogen. After heating at 115°C. for 10 hours, the reaction mixture is evaporated under reduced pressure and then hydrolyzed for 20 hours at 155°C with 13 milliliters of six normal hydrochloric acid. Analysis indicates the hydrolysate contains 0.39 grams of lysine and 0.54 grams of pipecolic acid, yields of 22 and 35%, respectively, based on 1-acetyl-2-cyanopiperidine. The overall yield of lysine based on 2-cyanopyridine is 11%.

EXAMPLE 2

The general procedure of Example 1 is followed, except that the 1-acetyl-2-cyanopiperidine is treated with (1) a nitrogen pressure of 500 psi instead of 200 psi, (2) twenty grams (ca. 0.45 moles) of carbon dioxide is used instead of 0.39 moles and (3) 15 ml. of six normal hydrochloric acid for 19½ hours, instead of 13 ml. of 6N.HCl for 20 hours.

The yields of lysine and pipecolic acid are 24 and 56% respectively. The overall yield of lysine from 2-cyanopyridine is 12%.

EXAMPLE 3

The general procedure of Example 1 is followed, except that the 1-acetyl-2-cyanopiperidine is reacted in the presence of 0.01 mole of ammonium cyanide in addition to the other reactants. The yield of lysine is greater than 29%.

We claim:

1. The method for the preparation of d,l-lysine which comprises hydrolyzing 2-cyanopyridine to picolinamide, hydrogenating the picolinamide to pipecolamide, converting the pipecolamide to 1-acetyl-2-cyanopiperidine with acetic anhydride, reacting 1-acetyl-2-cyanopiperidine with a compound which yields ammonium ions or a mixture thereof with a compound which yields carbonate ions and hydrolyzing the resulting product to d,l-lysine.

2. The method for the preparation of d,l-lysine which comprises hydrolyzing 2-cyanopyridine to picolinamide, hydrogenating the picolinamide to pipecolamide, converting the pipecolamide to 1-acetyl-2-cyanopiperidine with acetic anhydride, reacting 1-acetyl-2-cyanopiperidine with compounds which yield ammonium ions, compounds which yield carbonate ions or compounds which yield both ammonium and carbonate ions at a temperature in the range from about 60°C for a time sufficient to complete the reaction and hydrolyzing the reaction product at a temperature range from about 100° to 200°C to produce d,l-lysine.

3. The method as set forth in claim 2 wherein the compounds which yield ammonium ions are selected from the group consisting of ammonia, ammonium chloride, ammonium cyanide, and ammonium acetate.

4. The method as set forth in claim 2 wherein the compounds which yield carbonate ions are selected from the group consisting of carbon dioxide, sodium carbonate, sodium bicarbonate, potassium carbonate, and potassium bicarbonate.

5. The method as set forth in claim 2 wherein the compounds which yield both ammonium ions and carbonate ions are selected from the group consisting of ammonium carbonate, and ammonium bicarbonate.

6. The method as set forth in claim 2 in which the mole ratios of the compounds which yield ammonium ions to 1-acetyl-2-cyanopiperidine range from 3:1 to 50:1.

7. The method as set forth in claim 2 wherein the hydrolysis step is carried out in the presence of a strong acid.

8. The method as set forth in claim 2 wherein the hydrolysis step is carried out in the presence of a strong base.

* * * * *